US006951958B1

(12) United States Patent
Andersson et al.

(10) Patent No.: US 6,951,958 B1
(45) Date of Patent: Oct. 4, 2005

(54) SOLID PHASE PARALLEL SYNTHESIS OF TERTIARY AMINES

(75) Inventors: Carl-Magnus A. Andersson, Glostrup (DK); Magnus Gustafsson, Lund (SE); Kent R. I. Olsson, Malmo (SE)

(73) Assignee: Acadia Pharmaceuticals Inc., San Diego, CA (US)

( * ) Notice: Subject to any disclaimer, the term of this patent is extended or adjusted under 35 U.S.C. 154(b) by 384 days.

(21) Appl. No.: 10/049,669

(22) PCT Filed: Aug. 3, 2000

(86) PCT No.: PCT/US00/21225

§ 371 (c)(1),
(2), (4) Date: Nov. 22, 2002

(87) PCT Pub. No.: WO01/09081

PCT Pub. Date: Feb. 8, 2001

Related U.S. Application Data

(60) Provisional application No. 60/146,978, filed on Aug. 3, 1999.

(51) Int. Cl.$^7$ ............................................. C07C 211/00
(52) U.S. Cl. ....................... 564/384; 564/391; 564/462
(58) Field of Search ............................... 564/384, 391, 564/462

(56) References Cited

U.S. PATENT DOCUMENTS 6,133,409 A 10/2000 Salvino et al.

FOREIGN PATENT DOCUMENTS

| WO | WO 98/29376 | 7/1998 |
| WO | WO 99/09073 | 2/1999 |

OTHER PUBLICATIONS

Joseph M. Salvino, et al.: "Parallel Synthesis of Aldehydes and Ketone Facilitated by a New Solid-Phase Weinreb Amide", Journal of Organic Chemistry, vol. 64, No. 6, Mar. 19, 1999, pp. 1823-1830, XP002152402, American Chemical Society, Easton, US ISSN: 0022-3263 cited in the application p. 1824, col. 1, line 1—p. 1937, col. 2, line 26.
Angelo Liguori, et al.: "Novel Approach to the Ring-Opening Reaction of Isoxazolidinium Salts to 1,3-Amino Alcohols", Chemische Berichte, vol. 121, 1988, pp. 105-109, XP002152403, Weinheim, DE.; cited in the application p. 105, col. 1, line 1—p. 106, col. 2, line 18.
Eric E. Swayze, et al.: "The Synthesis of N, N'-O-Trisubstituted Hydroxylamines via a Mild Reductive Alkylation Procedure: An Improved Synthesis of the MMI Backbone"; Synlett, No. 7, Jul. 1997, paged 859-861, XP002152404, Thieme Verlag, Stuttgart, DE., ISSN: 0936-5214 cited in the application the whole document.

*Primary Examiner*—Samuel Barts
(74) *Attorney, Agent, or Firm*—Knobbe Martens Olson & Bear LLP

(57) ABSTRACT

Described is method for preparing tertiary amines comprising sequential, exhaustive alkylation of a hydroxylamine derivative and cleavage of the O—N bond using the following steps:
a) reacting the hydroxylamine derivative with an alkylating agent or with a carbonyl compound to form an oxime intermediate.
b) reacting the oxime intermediate with a reducing agent to produce an alkylated derivative
c) reacting the alkylated derivative with an alkylating agent or a carbonyl compound in the presence of a reducing agent to produce a dialkylated derivative
d) reacting the dialkylated derivative with an alkylating agent to produce a quaternized derivative
e) reacting the quaternized derivative with a reagent causing cleavage of the O—N bond to produce a tertiary amine.

34 Claims, 3 Drawing Sheets

SOLID PHASE PARALLEL SYNTHESIS OF TERTIARY AMINES

This application claims priority from U.S. Provisional Application 60/146,978, filed Aug. 3, 1999, which application is incorporated herein by reference.

FIELD OF THE INVENTION

The present invention relates to the synthesis of tertiary amines. More particularly a method of solid phase tertiary amine synthesis through sequential, exhaustive alkylation of a hydroxylamine derivative and cleavage of the N—O bond is described.

BACKGROUND OF THE INVENTION

Solid phase organic synthesis (SPOS) offers considerable advantages compared to traditional solution phase reactions. In particular, solid phase reactions are very attractive for combinatorial and parallel work because of the relative ease of purification of the resin bound material after each reaction step. Purification can be performed by simple washing and filtration. (see e.g., Obrecht and Villalgordo: Solid-Supported Combinatorial and Parallel Synthesis of Small-Molecular-Weight Compound Libraries, Pergamon, 1998).

Since virtually every endogenous and synthetic ligand that interacts with receptors in the central nervous system contains a basic functionality, most often a tertiary or secondary amino group, SPOS methods for the preparation of such compounds remains an extremely important aspect of medicinal chemistry aimed at central nervous system active drugs.

The solid phase organic synthesis of tertiary amines, using the nitrogen as the point of attachment to the solid support, is known in the art. (See FIG. 1) However, the methods described in previous work have disadvantages related to the lability of the linkers used as well as the release reactions.

SUMMARY OF THE INVENTION

Described is a new method for the solid phase synthesis of amines which comprises the linkage of an amino group via an N—O bond from resin-(linker)-O—NH$_2$. A series of reliable reactions are used for the introduction of all three R groups of the tertiary amine NR$^1$R$^2$R$^3$ (forming resin-(linker) O—N$^+$R$^1$R$^2$R$^3$). Finally, a novel release reaction, which delivers exclusively the material that has successfully undergone each of the previous synthetic steps, is performed. (Resin-linker-O—N$^+$R$^1$R$^2$R$^3$ gives N R$^1$R$^2$R$^3$). This type of release reaction, conditional release, serves to provide very pure product without any need for purification. The protocol is equally adaptable to split synthesis or linear parallel synthesis.

BRIEF DESCRIPTION OF THE DRAWINGS

The present invention may be better understood by reference to the appended figures and specification.

DETAILED DESCRIPTION OF THE INVENTION

Figure 1:
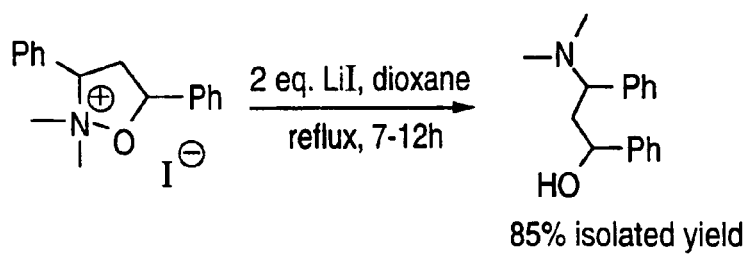
FIG. 1 illustrates the prior art conditional release reaction.
Figure 2A:
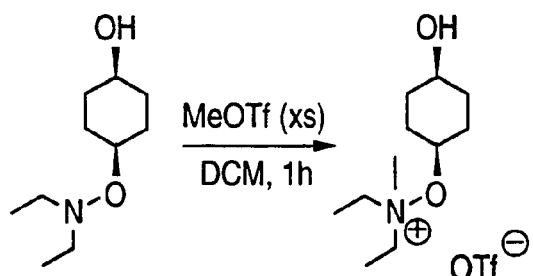
FIG. 2 illustrates the prior art alkylation reaction using alkoxyamine.
Figure 2B:
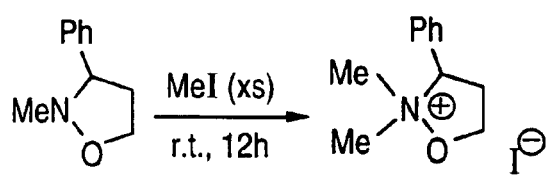
Figure 2C:
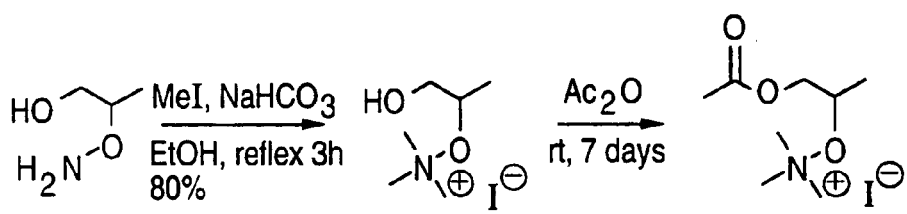
Figure 3:
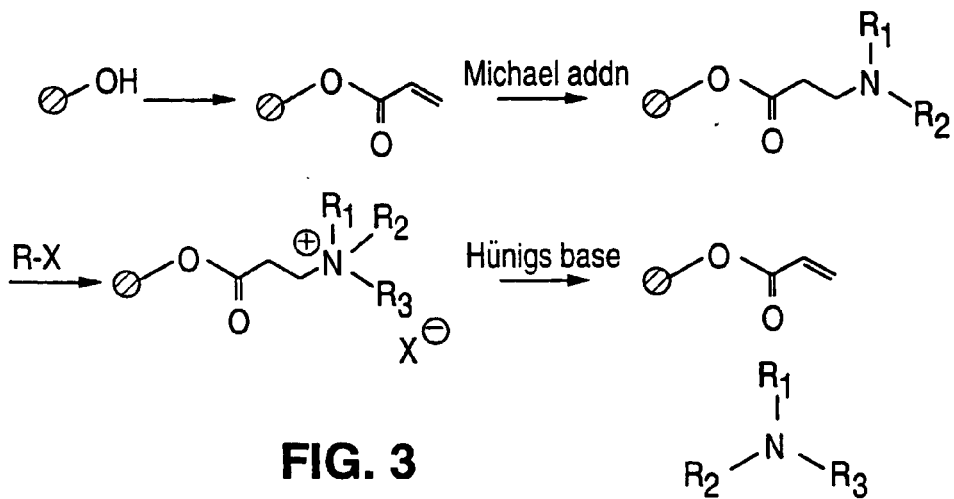
FIG. 3 illustrates alkoxyammonium ion cleavage
Figure 4:
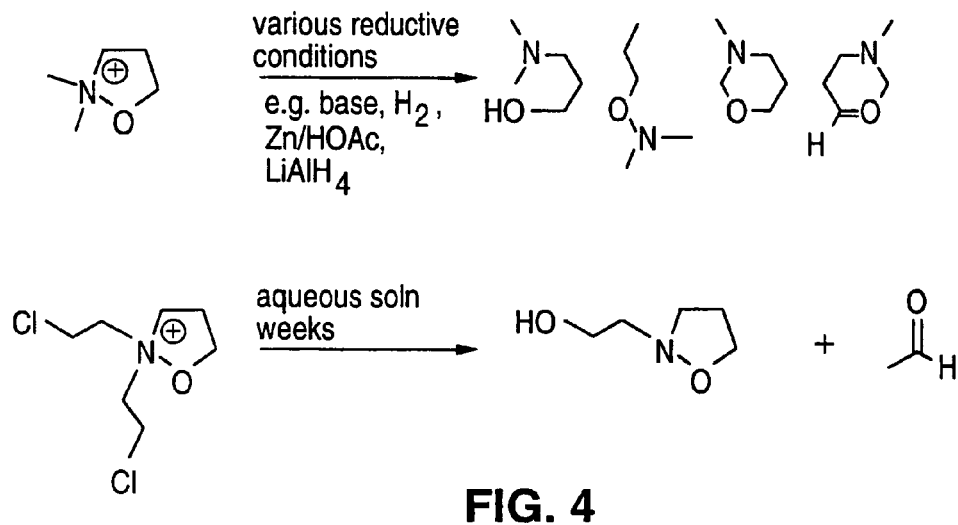
FIG. 4 illustrates alkoxyammonium ion reactivity in the prior art.
Figure 5:
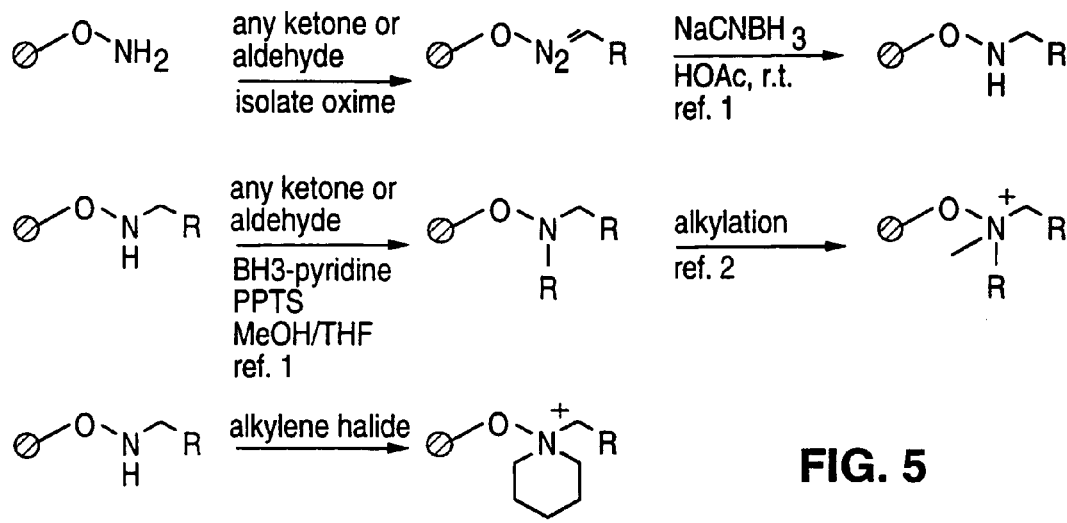
FIG. 5 illustrates reductive alkylation and alkylation as used in the prior art.
Figure 6:
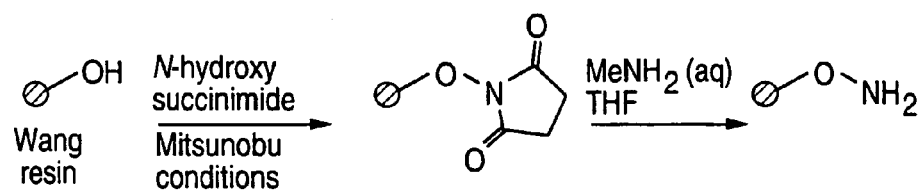
FIG. 6 illustrates the formation of a hydroxylamine resin
Figure 7:
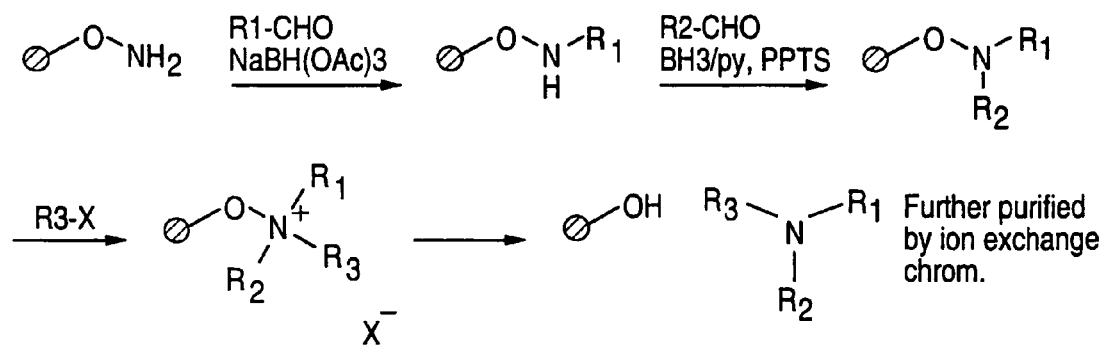
FIG. 7 illustrates the entire process of the presently described method.
Figure 8:
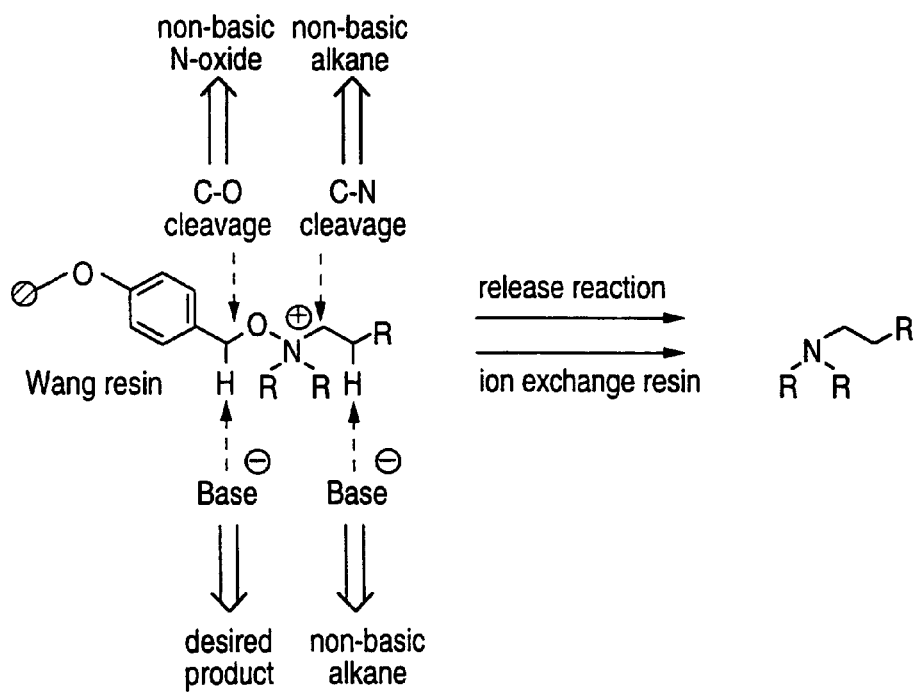
FIG. 8 illustrates the novel conditional release reaction.

Hydroxylamine resin may be prepared according to Salvino et al., or by attachment of a suitably protected hydroxylamine derivative to the desired resin, e.g. chloromethylated polystyrene or polystyrene grafted or functionalized with a suitable linker.

Introduction of the first R-group to the hydroxylamine resin is achieved either via alkylation or oxime formation followed by reduction. R may be any organyl group. More preferably R can be any cyclic, aromatic or acyclic organyl group.

Alkylation is performed by reacting the hydroxylamine derivative with an alkylating agent. Suitable alkylating agents are compounds carrying a nucleofuge such as organyl halides, tosylates or the like. In general alkylating agents may have the formula R—LG, wherein R is an organyl and LG is a nucleofuge.

In an alternative to alkylation, oxime formation can be run in one pot or the oxime may be isolated. Aromatic groups may be introduced, e.g., via palladium-catalyzed coupling between the resin and an aromatic or heteroaromatic halide or triflate. Any ketone or aldehyde serves to form an oxime with the resin. Many reducing agents can be used to reduce the oxime to the N-substituted hydroxylamine, including aluminum or boron complex hydrides.

The second R-group may again be any organyl group, and may be introduced via alkylation as described above. Alternately reductive amination may be used to introduce the second R group, wherein any aldehyde or ketone together with a suitable reducing agent is used.

The resin bound N,N-dialkylhydroxylamine derivative so obtained may be alkylated with any organic compound carrying a suitable nucleofuge, such as triflate, halide or tosylate, to form the cationic alkoxyammonium intermediate. This step introduces the third R-group.

Every step in the above sequence is easily driven to completion by the use of excess reagents and reactants and subsequent washing of the resin bound intermediate. Very high selectivity for the introduction of precisely one organyl group in each step (avoiding dialkylation) is achieved particularly effectively by performing oxime formation for the introduction of the first R-group, reduction, reductive amination for the introduction of the second R-group and alkylation for the introduction of the third R-group. This sequence of steps is preferred.

Extremely mild and exclusively conditional release is performed by treating the alkoxyammonium resin which has resulted from the above listed steps, with lithium iodide, preferably at elevated temperature. This reaction has been previously performed in solution by Liguori et al. However, the application of this very mild method for cleaving the N—O bond and thus releasing the desired organic product from the polymer support is novel, and serves to release selectively only material that has reacted in all the previous steps.

Furthermore, this method of release is tolerant to the presence of virtually any substituent in the product amine, since only modest temperatures and neutral conditions are used. Removal of the reagent lithium iodide can be performed by liquid-liquid or liquid-solid extraction, optionally in combination with further purification of the organic product NR"Alk$^1$Alk$^2$ via capture on acidic ion exchange resin, washing, and release as has been described by others. It is noticeable that this new linking strategy shows unprecedented selectivity for the release of only desired material, allows very mild conditions for assembly and cleavage of the amines and does not leave any compulsory functionality in the product; hence the linking is traceless.

The term organyl is used to denote any acyclic, alicyclic or heterocyclic, alkyl, alkenyl or alkynyl group, or an aromatic or heteroaromatic group. These groups may be branched or unbranched and may be optionally substituted with heteroatom-containing fragments, connected through either a heteroatom or a carbon atom.

A preferred embodiment of the inventive method disclosed comprises the following steps. Initially the hydroxylamine derivative PONH$_2$ is reacted with an alkylating agent having the formula R—LG or with a carbonyl compound having the formula RCOR' to form an oxime intermediate having the formula PON=CR'R. Most preferably the hydroxylamine derivative is reacted with a aldehyde or ketone. The resulting oxime intermediate is reacted with a reducing agent to produce an alkylated derivative, having the formula PONH(Alk$^1$). The alkylated derivative is reacted with an alkylating agent having the formula R—LG or a carbonyl compound having the formula RCOR' in the presence of a reducing agent to produce a dialkylated derivative having the formula PON(Alk$^1$)(Alk$^2$). Most preferably the alkylated derivative is reacted with a carbonyl compound. Even more preferably the carbonyl compound is an aldehyde or a ketone. The resultant dialkylated derivative is reacted with an alkylating agent having the formula R"—X to produce a quaternized derivative, having the formula PON$^+$R"(Alk$^1$)(Alk$^2$). Finally the quaternized derivative is reacted with a reagent which causes cleavage of the O—N bond to produce a tertiary amine having the formula NR"(Alk$^1$)(Alk$^2$). In this preferred embodiment of the method P is an organyl group or solid support, R is an organyl group, LG is a nucleofuge, R' is an organyl group or hydrogen, X is a nucleofuge, R" is an organyl group and Alk$^1$ and Alk$^2$ are the same or different and are each independently selected from the group consisting of R and CHRR'.

EXAMPLES

The examples given below are not intended to be limiting. Several modifications to the procedures described below are possible. The scope of the invention is limited by the appended claims only.

Examples are given below for the preparation of tertiary amines according to the method of the invention. The stepwise procedure is best exemplified by examples where the hydroxylamine derivative is soluble, i.e. P of the starting PONH$_2$ is an organyl group, since intermediates may be characterized in this case. In the solution phase examples below, P is benzyl. In the solid phase examples below, P is a modified Wang., Argogel, or Merrifield resin. During the latter experiments, reaction progress was monitored by solid-phase or gel-phase IR spectroscopy.

The methods and reagents employed for cleavage of the quaternized substrates PON$^+$R$_3$ are anticipated in the prior art, particularly in Liguori et. al. Chem. Ber. 1988, 121, 105–109 and in Liguori et. al. Tetrahedron 1984, 40, 1901–1906 and references cited therein. Methods for conducting other steps of the invention were also previously described in the art, for example in Swayze et. al. Synlett 1997, 859, Cannon et. al. J. Med. Chem. 1973, 16, 287, and Kano et. al. Tetrahedron 1992, 48, 10075, which discuss reductive aminations of relevance to the present invention, and in Salvino et. al. J. Org. Chem. 1999, 64, 1823 and Floyd et. al. Tetrahedron Lett. 1996, 37, 8045–8048 which both describe suitably modified resins. However, none of these procedures have been employed for the multi-step parallel preparation of tertiary amines, which is the subject matter disclosed in the present application.

Analysis of reaction products was performed using LC-MS and NMR spectroscopy. For LC-MS analyses, a HP 1100 LC-MSD system equipped with a binary pump and diode array detector was used. Mass spectral data were collected using an electrospray interface at positive mode, scanning from mass 80 to mass 700. The column was a Luna C18, 3 micrometer particle size, measuring 4.6×75 mm. A Phenomenex C18 4×3 mm guard column was used. The mobile phase consisted of A: 50% 8 mM ammoniumacetate/50% acetonitrile and B: 5% 8 mM ammoniumacetate/95% acetonitrile. A gradient program: 44.5% B at time 0 min increasing linearly to 100% B at time 11 min was used. The flowrate was 0.6 ml/min. Rt indicates retention times for the products under these experimental condition. NMR spectra were recorded on a 400 MHz apparatus.

Solution phase experiments (P=benzyl):

Example 1

Step (a), Introduction of (Alk$^1$)

Synthesis of O-(Benzyl)benzaldoxime(I)

A solution of O-(benzyl)hydroxylamine (1 eq.), benzaldehyde (1 eq.) and acetic acid (5% v/v in MeOH) was stirred for 15 h at rt. Aqueous workup and column chromatography gave I as a colorless oil. The product was identified using NMR spectroscopy, e.g. a peak at 8.18 ppm (singlet, HC=N) was diagnostic.

Example 2

Step (b), Introduction of (Alk$^1$)

Synthesis of N-Benzyl-O-(benzyl)hydroxylamine (II)

To a solution of I (1 eq.) and BH$_3$(pyridine) (4 eq.) in methanol was added HCl in dioxane (excess). The reaction mixture was stirred at rt for 12 h. Aqueous basic workup and column chromatography afforded II as a colorless oil. LC-MS: R=5.1 min.

Example 3

Step (c), Introduction of (Alk$^2$)

Synthesis of N-Isobutyl-N,O-dibenzylhydroxylamine (III)

To a solution of II (1 eq.), 2-methylpropanal (1 eq.) and BH$_3$(pyridine) (1 eq.) in THF:MeOH (1:3) was added PPTS (1 eq.). The reaction mixture was stirred at rt for 12 h and afforded, after aqueous workup and purification by column chromatography, III as a colorless oil.

LC-MS: Rt=11.3 min.

Example 4

Step (d), Introduction of (R")

Quaternization of III to Give IV

To a solution of III (1 eq.) in $CH_2Cl_2$ was added $Na_2CO_3$ (excess) and MeOTf (5 eq.). The reaction mixture was stirred at rt for 15 h. Evaporation of excess MeOTf and $CH_2Cl_2$ afforded a mixture of $Na_2CO_3$ and IV. Extraction with EtOH afforded the product as a white solid after evaporation.

Analysis by NMR confirmed the identity of the product, e.g. a diagnostic peak at 3.6 ppm (singlet, $N^+Me$).

Similar reactions excluding $Na_2CO_3$ were also effective.

Example 5

Step (e), Cleavage

Synthesis of N-Benzyl-N-isobutyl-N-methylamine (V)

To a solution of IV in dioxane or MeCN was added LiI (2 eq.). The reaction mixture was heated for 12 h at 70° C. Aqueous workup and purification through an ion exchange column (Isolute SCX) afforded V. LC-MS: Rt=5.8 min. Similar cleavages of compound IV were effected using $Et_3N$ in $CH_2Cl_2$, $K_2CO_3$ in DMF or $SmI_2$ in THF.

Solid phase experiments (P=solid support):

Synthesis of a hydroxylamine substrate $PONH_2$ (P=solid support) from Argogel resin was conducted in analogy with the procedure in Salvino et. al. J. Org. Chem. 1999, 64, 1823, which provided the required polystyrene-polyethylene glycol-$ONH_2$ resin (VI).

Example 6

Step (a), Introduction of (Alk$^1$)

Oxime resin (VII)

Resin VI was swollen in THF:MeOH (2:1) for 5 min. Cyclohexylcarboxaldehyde (excess) and HOAc were added. The mixture was stirred at rt for 150 h. The resin was filtered and washed with THF and MeOH followed by drying at 40° C. under vacuo.

Example 7

Step (a), Introduction of (Alk$^1$)

Hydroxylamine resin (VIII)

To oxime resin VII in THF:MeOH (1:1) were added $BH_3$(pyridine) and HCl in dioxane (both in excess). The reaction mixture was shaken at rt for 15 h, filtered and washed with $Et_3N$ in MeOH and then MeOH and finally dried in vacuo.

Example 8

Step (b), Introduction of (Alk$^2$)

Hydroxylamine resin (IX)

To resin VIII in THF:MeOH (3:1) was added 2-methylpropanal (excess), $BH_3$(pyridine) (excess) and PPTS (excess). The reaction mixture was shaken at rt for 12 h, filtered and washed with MeOH and THF followed by drying under vacuo.

Example 9

Step (c), Introduction of (R")

Quaternization of hydroxylamine resin IX

To resin IX in $CH_2Cl_2$ was added MeOTf (excess). The reaction mixture was shaken at rt for 12 h, filtered, washed with $CH_2Cl_2$ and dried under vacuo to provide the quaternized resin X.

Example 10

Step (d), Cleavage

Preparation of N-Cyclohexylmethyl-N-isobutyl-N-methylamine

Quaternized resin X, prepared above, when subjected to any of the conditions given in Example 5 above, released the desired amine, N-Cyclohexylmethyl-N-isobutyl-N-methylamine.

We claim:

1. A method for preparing tertiary amines comprising:
   sequential, exhaustive alkylation of a hydroxylamine derivative; and,
   cleavage of the O—N bond.

2. The method of claim 1 wherein the sequential, exhaustive alkylation of a hydroxylamine derivative of the formula $PONH_2$ comprises the steps of:
   a) forming an alkylated derivative, having the formula PONH(Alk$^1$), by reacting the hydroxylamine derivative with
      an alkylating agent having the formula R—X,
      or a carbonyl compound having the formula RCOR' to form an oxime intermediate having the formula PON=CR'R and reacting the oxime intermediate with a reducing agent;
   b) forming a dialkylated derivative having the formula PON(Alk$^1$)(Alk$^2$) by reacting the alkylated derivative with
      an alkylating agent having the formula R—LG,
      or a carbonyl compound having the formula RCOR' in the presence of a reducing agent; and,
   c) reacting the dialkylated derivative with an alkylating agent having the formula R"—X' to produce a quaternized derivative, having the formula PON$^+$R"(Alk$^1$)(Alk$^2$), wherein P is an organyl group or solid support, R is an organyl group, R' is an organyl group or hydrogen, R" is an organyl group, X and X' are each a nucleofuge, and Alk$^1$ and Alk$^2$ are the same or different and are each independently selected from the group consisting of R and CHRR'.

3. The method of claim 2 wherein P is a solid support.

4. The method of claim 2 wherein P is grafted or functionalized polystyrene.

5. The method of claim 2 wherein P is selected from the group consisting of Wang resin, Argogel resin, Merrifield resin and Tentagel resin.

6. The method of claim 2, wherein P is benzyl.

7. The method of claim 2 wherein the alkylating agents are selected from the group consisting of primary organyl chloride, bromide, iodide, tosylate, mesylate and triflate.

8. The method of claim 2 wherein the reducing agent is a complex hydride reagent.

9. The method of claim 8 wherein the reducing agent is applied under acidic conditions.

10. The method of claim 2 wherein the reducing agent is selected from the group consisting of $BH_3$(pyridine), NaCNBH$_3$, NaBH$_4$, Na(OAc)$_3$BH, Zn(BH$_4$)$_2$, and B$_2$H$_6$.

11. The method of claim 2 where X is triflate.

12. The method of claim 2 wherein step b) is performed using a carbonyl compound and wherein the carbonyl compound is an aldehyde or ketone.

13. The method of claim 2 wherein step d) is performed using a bifunctional reagent, such that R" and (Alk$^2$) of the quaternized derivative form a ring.

14. The method of claim 13 wherein the ring contains 4, 5, or 6 carbon atoms.

15. The method described in claim 1, wherein the sequential, exhaustive alkylation of a hydroxylamine derivative produces a quaternized derivative having the formula PON$^+$R"(Alk$^1$)(Alk$^2$), and wherein cleavage of the O—N bond comprises reacting the quaternized derivative with a reagent causing cleavage of the O—N bond to produce a tertiary amine having the formula NR"(Alk$^1$)(Alk$^2$) where R" is an organyl and Alk$^1$ and Alk$^2$ are the same or different and are each independently selected from the group consisting of R and CHRR'.

16. The method of claim 15 wherein the reagent is iodide ion or a base.

17. The method of claim 15 wherein the reagent is samarium iodide or lithium iodide.

18. The method of claim 15 wherein the reagent is a trialkyl amine or carbonate.

19. A method for preparing tertiary amines comprising:
a) forming an alkylated derivative, having the formula PONH(Alk$^1$), by reacting the hydroxylamine derivative with
an alkylating agent having the formula R—X,
or a carbonyl compound having the formula RCOR' to form an oxime intermediate having the formula PON=CR'R and reacting the oxime intermediate with a reducing agent;
b) forming a dialkylated derivative having the formula PON(Alk$^1$)(Alk$^2$) by reacting the alkylated derivative with
an alkylating agent having the formula R—LG,
or a carbonyl compound having the formula RCOR' in the presence of a reducing agent; and,
c) reacting the dialkylated derivative with an alkylating agent having the formula R"—X' to produce a quaternized derivative, having the formula PON$^+$R"(Alk$^1$)(Alk$^2$); and,
d) reacting the quaternized derivative with a reagent causing cleavage of the O—N bond to produce a tertiary amine having the formula NR"(Alk$^1$)(Alk$^2$);
wherein P is an organyl group or solid support, R is an organyl group, R' is an organyl group or hydrogen, R" is an organyl group, X and X' are the same or different and are each a nucleofuge, and Alk$^1$ and Alk$^2$ are the same or different and are each independently selected from the group consisting of R and CHRR'.

20. The method of claim 19 wherein P is grafted or functionalized polystyrene, the hydroxylamine derivative is reacted with a carbonyl compound and the alkylated derivative is reacted with a carbonyl compound, the reducing agent is $BH_3$(pyridine), NaCNBH$_3$, or Na(OAc)$_3$BH, R" is a methyl group, X is triflate, and the reagent is iodide ion or a base.

21. The method of claim 19 wherein P is a solid support.

22. The method of claim 19 wherein P is grafted or functionalized polystyrene.

23. The method of claim 19 wherein P is selected from the group consisting of Wang resin, Argogel resin, Merrifield resin and Tentagel resin.

24. The method of claim 19 wherein P is benzyl.

25. The method of claim 19 wherein the alkylating agents are selected from the group consisting of primary organyl chloride, bromide, iodide, tosylate, mesylate and triflate.

26. The method of claim 19 wherein the reducing agent is a complex hydride reagent.

27. The method of claim 26 wherein the reducing agent is applied under acidic conditions.

28. The method of claim 19 wherein the reducing agent is selected from the group consisting of $BH_3$(pyridine), NaCNBH$_3$, NaBH$_4$, Na(OAc)$_3$BH, Zn(BH$_4$)$_2$, and B$_2$H$_6$.

29. The method of claim 19 where X is triflate.

30. The method of claim 19 wherein step d) is performed using a bifunctional reagent, such that R" and (Alk$^2$) of the quaternized derivative form a ring.

31. The method of claim 30 wherein the ring contains 4, 5, or 6 carbon atoms.

32. The method of claim 19 wherein the reagent is iodide ion or a base.

33. The method of claim 19 wherein the reagent is samarium iodide or lithium iodide.

34. The method of claim 19 wherein the reagent is a trialkyl amine or carbonate.

* * * * *